(12) United States Patent
Fujita

(10) Patent No.: US 6,649,400 B2
(45) Date of Patent: Nov. 18, 2003

(54) BACTERIA MIXTURE HAVING HEAVY OIL DEGRADING ABILITY AND METHOD OF TREATING OIL COMPONENTS

(75) Inventor: Tokio Fujita, Nara (JP)

(73) Assignee: Technology Licensing Organization Inc., Osaka (JP)

(*) Notice: Subject to any disclaimer, the term of this patent is extended or adjusted under 35 U.S.C. 154(b) by 0 days.

(21) Appl. No.: 09/518,814

(22) Filed: Mar. 3, 2000

(65) Prior Publication Data

US 2003/0036187 A1 Feb. 20, 2003

(30) Foreign Application Priority Data

Mar. 29, 1999 (JP) .............................. 11-087162

(51) Int. Cl.$^7$ .............................. C12N 1/20; C10G 32/00
(52) U.S. Cl. .................. 435/252.4; 435/281; 435/262.5
(58) Field of Search ........................... 435/262.5, 252.4, 435/281

(56) References Cited

U.S. PATENT DOCUMENTS

| | | | |
|---|---|---|---|
| 3,813,316 A | 5/1974 | Chakrabarty | |
| 4,259,444 A | 3/1981 | Chakrabarty | ................ 435/172 |

FOREIGN PATENT DOCUMENTS

| | | |
|---|---|---|
| CA | 2136628 | 12/1993 |
| CA | 2229761 | 9/1998 |
| EP | 0 077 422 A1 | 4/1983 |
| EP | 0 668 246 A1 | 8/1995 |
| FR | 2 187 911 A | 1/1974 |
| GB | 1 111 804 A | 5/1968 |
| GB | 2 084 608 A | 4/1982 |
| JP | 5-344880 | 12/1993 |
| JP | 07008270 | 1/1995 |
| JP | 07023773 | 1/1995 |
| JP | 7095878 | 4/1995 |
| JP | 07095878 | 4/1995 |
| JP | 07-123978 | 5/1995 |
| JP | 10008071 | 1/1998 |
| JP | 10-276771 | 10/1998 |
| WO | WO 92/19373 | 11/1992 |

OTHER PUBLICATIONS

Butt et al., Pak J Zool, (1988) 20 (4), 391–400.*
Bobra, et al., Environ. Sci. Res. (1980), Volume Date 1978, 16(Hydrocarbons Halogenated Hydrocarbons Aquat. Environ.), 521–30.*
Benka–Coker, et al., Environ. Monit. Assess. (1997), 45(3), 259–272.*
Amin, et al., Al–Azhar J. Microbiol. (1997), 36, 1–10.*
Fuenmayor et al., Acta Cient. Venez. (1992), 43(6), 349–54.*
Caldini, et al., Appl. Microbiol. Biotechnol. (1995), 44(1–2), 225–9.*
Venkateswaran, K., et al., "Distribution and biodegradation potential of oil–degrading bacteria in North Eastern Japanese Coastal Waters" FEMS Microbiology Ecology, vol. 86, 1991, pp. 113–122.
Amund, O., et al., "Microbial degradation of four Nigerian crude oils in an estuarine microcosm" Letters in Applied Microbiology, vol. 16, 1993, pp. 118–121.

* cited by examiner

*Primary Examiner*—Irene Marx
(74) *Attorney, Agent, or Firm*—Edwards & Angell; Cara Z. Lowen

(57) ABSTRACT

A bacteria strain FERMBP-7046 belonging to the genus Acinetobacter, a strain FERMBP-7049 belonging to the genus Acinetobacter, a strain FERMBP-7047 belonging to the genus Pseudomonas, and a strain FERMBP-7048 belonging to the genus Alcaligenes are caused to act on an object of treatment, either individually or in a bacteria mixture including at least one of the foregoing strains. Thus it is possible to provide heavy oil degrading bacteria and a heavy oil degrading bacteria mixture which are inexpensively prepared, which simplify degradation and removal operations, and which can be stored and shipped simply, and to provide a nurturing composition for such bacteria, a method of degrading heavy oil using such bacteria, and building and civil engineering materials containing a substance obtained by heavy oil degradation treatment.

7 Claims, 5 Drawing Sheets

RETENTION TIME (MINUTES)

RETENTION TIME (MINUTES)

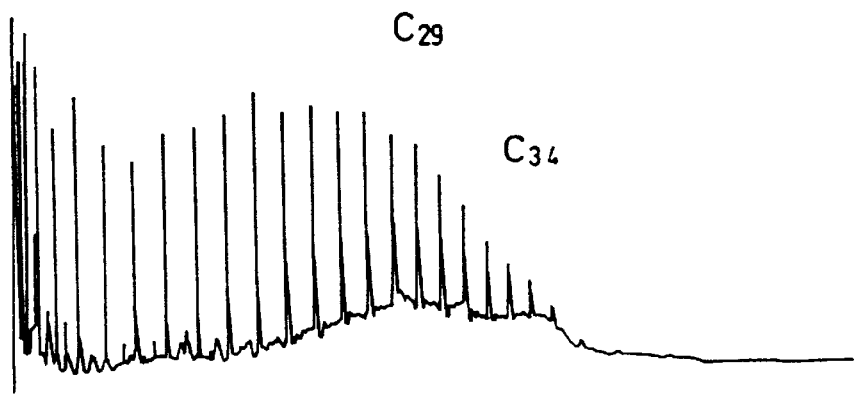
FIG.3(a)
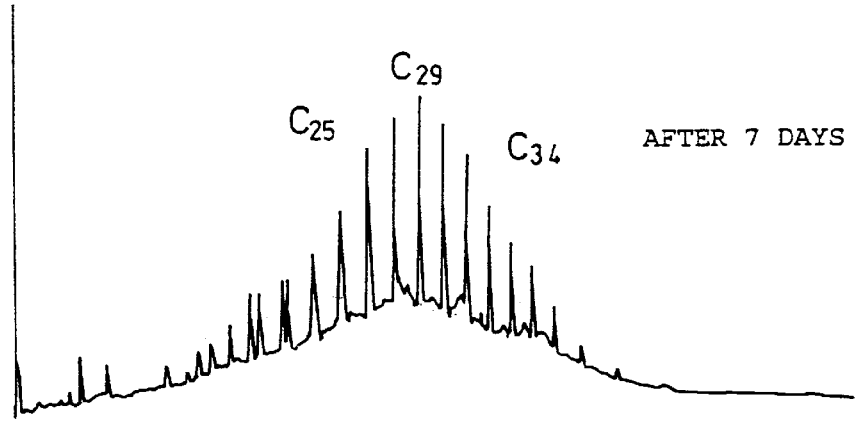
FIG.3(b) AFTER 7 DAYS
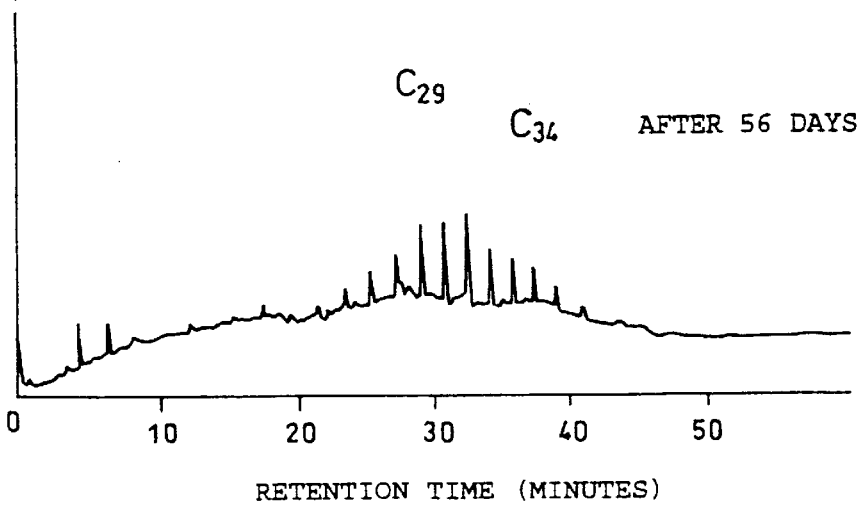
FIG.3(c) AFTER 56 DAYS
RETENTION TIME (MINUTES)

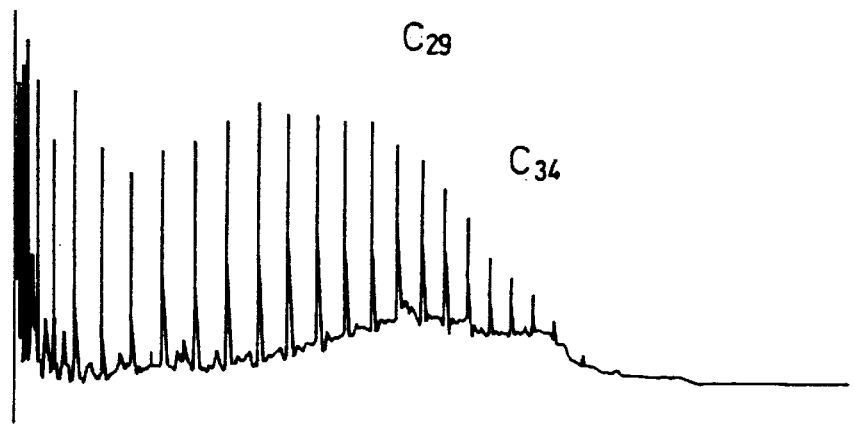
FIG.4(a)
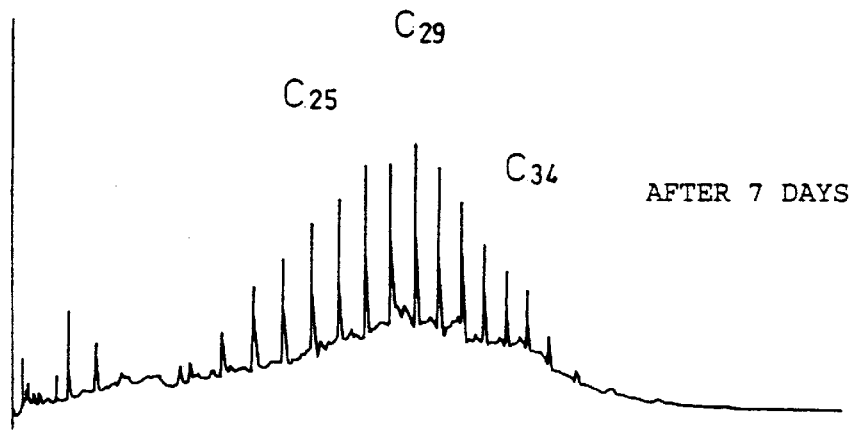
FIG.4(b) AFTER 7 DAYS
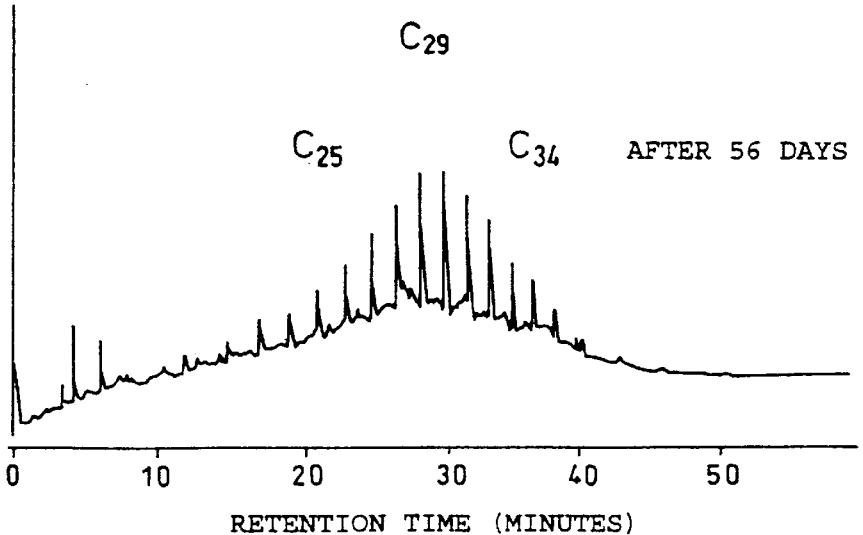
FIG.4(c) AFTER 56 DAYS
RETENTION TIME (MINUTES)

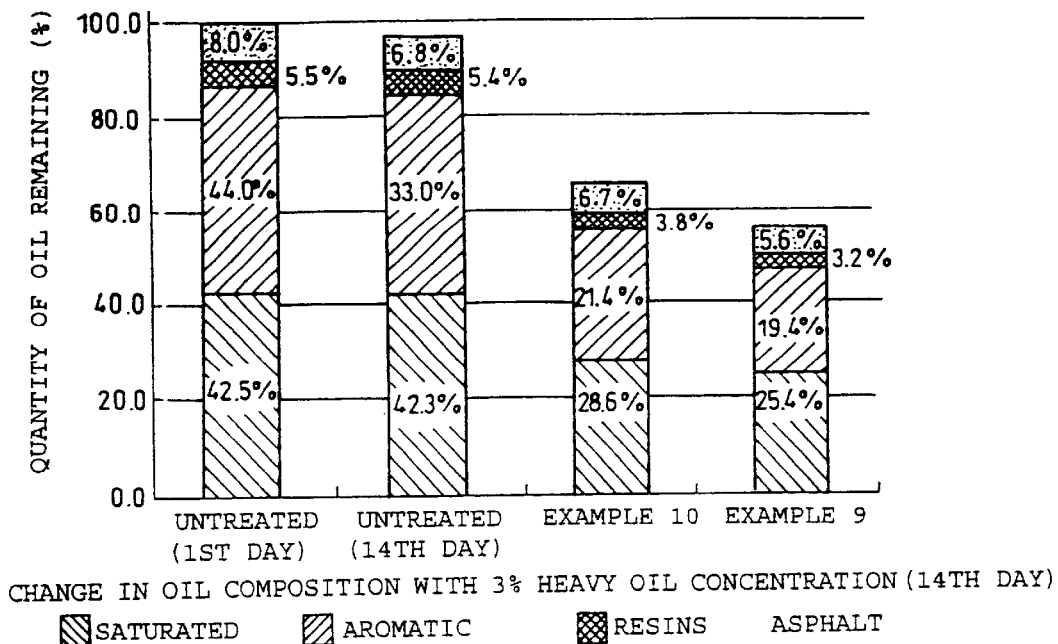
CHANGE IN OIL COMPOSITION WITH 3% HEAVY OIL CONCENTRATION (14TH DAY)
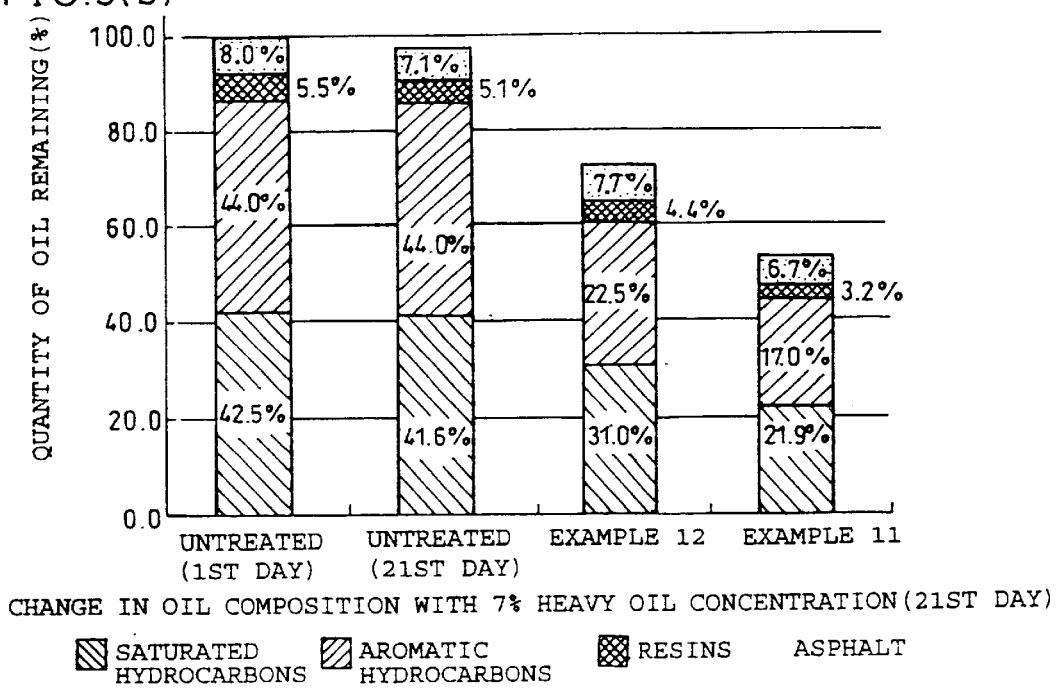
CHANGE IN OIL COMPOSITION WITH 7% HEAVY OIL CONCENTRATION (21ST DAY)

BACTERIA MIXTURE HAVING HEAVY OIL DEGRADING ABILITY AND METHOD OF TREATING OIL COMPONENTS

FIELD OF THE INVENTION

The present invention relates to a novel strain of bacteria for use in heavy oil degradation, a bacteria mixture, a composition for nurturing heavy oil degrading bacteria, a formulation containing that composition, a method of treating oil components, and building and civil engineering materials containing a substance treated by that method.

BACKGROUND OF THE INVENTION

Recent years have seen worsening of ocean pollution throughout the world due to heavy oil or crude oil leaks from supertanker accidents, submarine oil field development, etc., and this is one cause of damage to the global environment.

Conventionally, oils, such as heavy oil and crude oil, leaked into the ocean are removed through degradation by microorganisms capable of degrading chiefly hydrocarbons contained in the oils. Specifically, microorganisms which can metabolize and degrade oil components such as saturated hydrocarbons, aromatic hydrocarbons, etc. are screened from the natural world, and the screened microorganisms are isolated and grown, after which a culture solution is prepared for use in degradation of the leaked oil.

In addition, if the microorganisms are provided with nutrients necessary to grow during the degrading and removing process, the microbes are able to exercise their degrading ability to the full. Alternatively, instead of a combination of microorganisms and nutrients, nutrients alone may be added to the object of treatment (e.g. heavy oil), so that the oil is removed through degradation by other kinds of microorganisms having the degrading ability originally present in the vicinity of the object.

For example, bacteria having a hydrocarbon degrading ability are ordinarily present at the seashore. Thus, if the hydrocarbon degrading ability the bacteria inherently possess is activated by providing the bacteria with nutrients, the e.g. heavy oil can be removed through degradation in an ecologically benign manner, which is advantageous for environmental protection.

On the other hand, in order to degrade and remove heavy oil leaked from a supertanker accident, for example, earth and sand with the heavy oil attached thereto are often treated without first being separated from the heavy oil. For example, if heavy oil washed ashore is to be removed through degradation on the seashore, the heavy oil and the earth and sand are generally not separated from each other before degradation and removal processing.

However, when oil, etc. is removed through degradation using microorganisms having the ability to degrade e.g. hydrocarbons in the above conventional manner, growth conditions for the microorganisms must be adjusted by providing various kinds of nutrients.

In other words, in degrading and removing oil components using microorganisms, it is most effective to use living bacteria in a steady period, which is when they show their ability to degrade e.g. hydrocarbons to the fullest. However, in order to use the growing bacteria in the steady period, a culture solution containing expensive nutrients must be prepared, and setting growth conditions precisely requires tedious and time-consuming operations. Specifically, a huge quantity of live bacteria are necessary to remove heavy oil through degradation. Hence, if the required quantity or cost of the nutrients (nutrient salts) per unit volume of the culture solution is high, there arises the problem that costs are too high. Further, too much labor is required to control the growing period.

Also, in order to use live bacteria in a culture solution in degradation, special facilities are required in the storage, shipping, etc. of the culture solution, thus making preparations and operations too complicated.

On the other hand, using microorganisms to degrade and remove heavy oil from earth and sand with heavy oil attached thereto without first separating the heavy oil from the earth and sand also has the problem that further costs are incurred in disposal of the treated earth and sand, which contain degradation products and residual components such as asphalt.

SUMMARY OF THE INVENTION

It is an object of the present invention to provide heavy oil degrading bacteria and a heavy oil degrading bacteria mixture which are inexpensively prepared, which simplify degradation and removal operations, and which can be stored and shipped simply, and to provide a nurturing composition for such bacteria, a method of degrading heavy oil using such bacteria, a method of treating oil components using such bacteria, and building and civil engineering materials containing a substance obtained by heavy oil degradation treatment.

In order to achieve the above object, the inventors of the present invention conducted an assiduous study, and completed the present invention when they discovered that the above object can be achieved by using strains of bacteria collected from seawater by means of screening, and a mixture thereof.

Novel strains of bacteria according to the present invention which have a heavy oil degrading ability and can achieve the above object are FERMBP-7046, a strain belonging to the genus Acinetobacter; FERMBP-7049, a strain belonging to the genus Acinetobacter; FERMBP-7047, a strain belonging to the genus Pseudomonas; FERMBP-7048, a strain belonging to the genus Alcaligenes; FERMBP-7050, a strain belonging to the genus Flavobacterium; FERMBP-7051, a strain belonging to the genus Flavobacterium; FERMBP-7052, a strain belonging to the genus Flavobacterium; and FERMBP-7053, a strain belonging to the genus Moraxella.

A bacteria mixture according to the present invention which can achieve the above object is a bacteria mixture including at least one kind of bacteria having a heavy oil degrading ability selected from the group consisting of: FERMBP-7046, a strain of Acinetobacter; FERMBP-7049, a strain of Acinetobacter; FERMBP-7047, a strain of Pseudomonas; FERMBP-7048, a strain of Alcaligenes; FERMBP-7050, a strain of Flavobacterium; FERMBP-7051, a strain of Flavobacterium; FERMBP-7052, a strain of Flavobacterium; and FERMBP-7053, a strain of Moraxella.

The foregoing bacteria or bacteria mixture was discovered when bacteria were isolated from seawater in order to discover a strain having a hydrocarbon degrading ability in nutrient-poor conditions as close as possible to those in the natural world. Thus, the above bacteria or bacteria mixture can be readily grown on inexpensive nutrition sources and degrade hydrocarbon efficiently. Accordingly, leaked oil components, for example, can be easily and efficiently removed through degradation at a low cost by using the foregoing bacteria or bacteria mixture.

In particular, the above bacteria mixture shows a better ability to degrade oil components than when each of the foregoing kinds of bacteria is used alone, and for this reason, heavy oil can be removed through degradation more efficiently by using the above bacteria mixture.

In addition, degradation of heavy oil can be further promoted when the bacteria mixture also includes at least one of FERMBP-7050, a strain of Flavobacterium; FERMBP-7051, a strain of Flavobacterium; FERMBP-7052, a strain of Flavobacterium; and FERMBP-7053, a strain of Moraxella.

Additional objects, features, and strengths of the present invention will be made clear by the description below. Further, the advantages of the present invention will be evident from the following explanation in reference to the drawings.

BRIEF DESCRIPTION OF THE DRAWINGS

FIG. 3(a) is an explanatory drawing showing an elution pattern obtained by gas chromatography analysis, which illustrates change over time of a saturated hydrocarbon fraction due to the action of a bacteria mixture and a heavy oil degrading bacteria nurturing composition according to the present invention on sand with 3% by weight of heavy oil attached thereto.

FIG. 3(b) is an explanatory drawing showing an elution pattern obtained by gas chromatography analysis, which illustrates change over time of a saturated hydrocarbon fraction due to the action of a bacteria mixture and a heavy oil degrading bacteria nurturing composition according to the present invention on sand with 3% by weight of heavy oil attached thereto.

FIG. 3(c) is an explanatory drawing showing an elution pattern obtained by gas chromatography analysis, which illustrates change over time of a saturated hydrocarbon fraction due to the action of a bacteria mixture and a heavy oil degrading bacteria nurturing composition according to the present invention on sand with 3% by weight of heavy oil attached thereto.

FIG. 4(a) is an explanatory drawing showing an elution pattern obtained by gas chromatography analysis, which illustrates change over time of a saturated hydrocarbon fraction due to the action of a heavy oil degrading bacteria nurturing composition according to the present invention on sand with 3% by weight of heavy oil attached thereto.

FIG. 4(b) is an explanatory drawing showing an elution pattern obtained by gas chromatography analysis, which illustrates change over time of a saturated hydrocarbon fraction due to the action of a heavy oil degrading bacteria nurturing composition according to the present invention on sand with 3% by weight of heavy oil attached thereto.

FIG. 4(c) is an explanatory drawing showing an elution pattern obtained by gas chromatography analysis, which illustrates change over time of a saturated hydrocarbon fraction due to the action of a heavy oil degrading bacteria nurturing composition according to the present invention on sand with 3% by weight of heavy oil attached thereto.

FIG. 5(a) is a graph explaining change in composition of heavy oil components due to treatment of sand with 3% by weight of heavy oil attached thereto using a bacteria mixture or a heavy oil degrading bacteria nurturing composition according to the present invention.

FIG. 5(b) is a graph explaining change in composition of heavy oil components due to treatment of sand with 7% by weight of heavy oil attached thereto using a bacteria mixture or a heavy oil degrading bacteria nurturing composition according to the present invention.

DESCRIPTION OF THE EMBODIMENTS

Figure 1A:
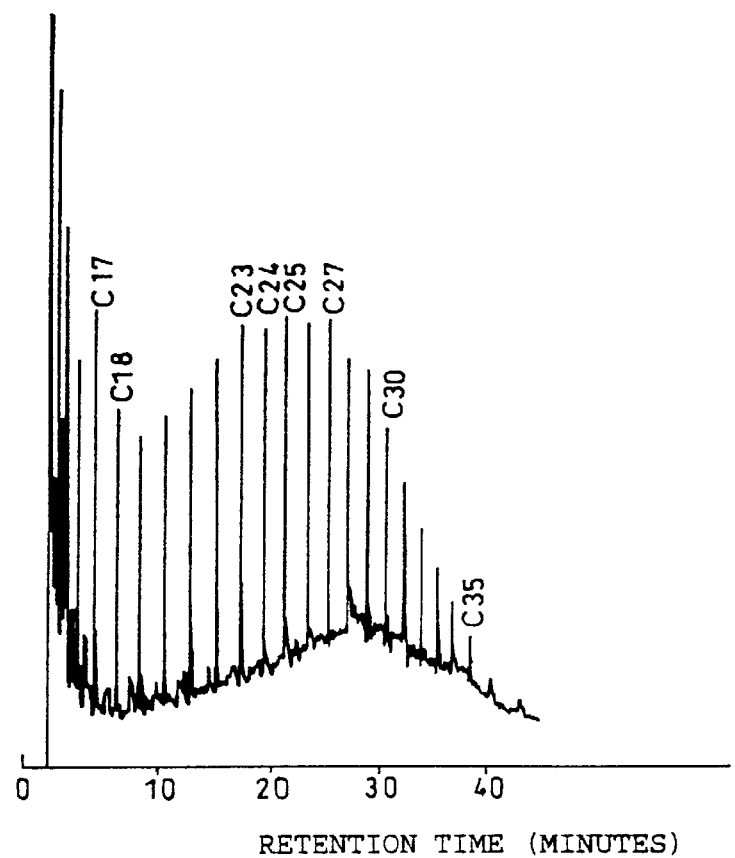
FIG. 1(a) is an explanatory drawing showing an elution pattern obtained by gas chromatography analysis, which illustrates degradation and removal of saturated hydrocarbon components contained in heavy oil by a bacteria mixture according to the present invention, showing the state before degradation.

The following will explain an embodiment of the present invention with reference to the drawings.

First Embodiment

Each of the bacteria strains according to the present invention, i.e. FERMBP-7046, a strain belonging to the genus Acinetobacter; FERMBP-7049, a strain belonging to the genus Acinetobacter; FERMBP-7047, a strain belonging to the genus Pseudomonas; and FERMBP-7048, a strain belonging to the genus Alcaligenes, is a novel strain collected from the natural world by means of screening, and each was isolated as a useful microorganism having the ability to degrade hydrocarbons, for example to degrade oil components, such as heavy oil.

In the present invention, "ability to degrade heavy oil" means not only an ability to degrade relatively high-molecule hydrocarbons contained in the heavy oil, but also an ability to degrade relatively low-molecule hydrocarbons resulting from degradation of the foregoing relatively high-molecule hydrocarbons.

In addition, a bacteria mixture including at least one bacteria strain selected from the group consisting of the foregoing four strains, and this bacteria mixture further including a bacteria group consisting of a strain belonging to the genus Flavobacterium and/or a strain belonging to the genus Acinetobacter shows even better hydrocarbon degrading ability than the above four kinds of strains when each is added separately to the object of treatment.

The following will explain the process by which the bacteria of the present invention were isolated.

The Acinetobacter strain FERMBP-7046 (TFBOL-1), the Acinetobacter strain FERMBP-7049 (TFBOL-7), the Pseudomonas strain FERMBP-7047 (TFBOL-2), and the Alcaligenes strain FERMBP-7048 (TFBOL-3) of the present invention are bacteria which were isolated from natural seawater.

The first screening was carried out in the following manner.

A culture medium having the composition set forth in Table 1 below was used as an isolating culture medium for isolating bacteria from a total of 50 samples of seawater, water, and sediment collected from harbors, offshore waters, and rivers throughout Japan. This composition was used because the carbon source used was fluid paraffin (nacalai tesque K.K.), in order to isolate strains having a hydrocarbon degrading ability under nutrient-poor conditions as close as possible to those in the natural world. Here, fluid paraffin is defined as a saturated hydrocarbon mixture having 15–30 carbon atoms.

TABLE 1

| | |
|---|---|
| FLUID PARAFFIN (LIGHT) | 10.0 g |
| AMMONIUM CHLORIDE | 100 mg |
| POTASSIUM PHOSPHATE MONOBASIC | 10 mg |
| DISTILLED WATER (OR SEAWATER) | 1000 ml |
| pH | 6.5–7.0 |

Each of the foregoing samples of seawater, etc. was isolated by means of filtration (pore diameter: 0.45 $\mu$m), and 1 ml (in case of liquid filtrate) or 1 g (in case of solid filtrate) of the sample was added to a 500-ml shaking flask with 100 ml of the foregoing isolating culture medium which had been sterilized by wet heat sterilization (121° C.; 20 min.)

The mixture of the sample and isolating culture medium was cultured by shaking (120 strokes/min.; 5 cm; 30° C.) for 7–10 days, and an accumulation culture was conducted by planting 1 ml of the culture solution to a new isolating culture medium a total of four times in succession. The microorganisms present in the fourth accumulative culture solution obtained thereby were mixed saturated hydrocarbon degrading bacteria.

Then the second screening was carried out in the following manner. The foregoing accumulative culture solution containing the mixed bacteria was mixed with the isolating culture medium at a volume ratio of 1:1, and the resulting mixture was cultured by shaking (120 strokes/min.; 5 cm; 30° C.), and then visually observed. A culture solution in which the emulsification and dispersion rates of the fluid paraffin were observed to be at or above their respective predetermined rates, and having the lowest observed n-hexane extract fraction quantity after seven days of culturing, was obtained as an excellent mixed strain. The following will explain in detail the second screening.

First, the mixed saturated hydrocarbon degrading bacteria obtained by the foregoing accumulation culture were cultured by shaking (120 strokes/min.; 5 cm; 25° C.) for four days in a preparatory culture medium having the composition set forth in Table 2 below, yielding a preparatory culture solution, from which bacteria were collected by centrifuge separation (3500 rpm; 20 min.). Then the collected bacteria were washed twice with the preparatory culture medium, yielding 1 ml of a bacteria suspension. Next, 1 ml of the foregoing bacteria suspension (bacteria count: $10^9$/ml) was inoculated into a 500-ml shaking flask containing 100 ml of a basic salt culture medium having the composition set forth in Table 3 below, and cultured by shaking (120 strokes/min.; 5 cm; 30° C.).

TABLE 2

| | |
|---|---|
| FLUID PARAFFIN (LIGHT) | 10.0 g |
| MAGNESIUM SULFATE HEPTAHYDRATE | 0.2 g |
| CALCIUM CHLORIDE | 0.02 g |
| POTASSIUM PHOSPHATE MONOBASIC | 1.0 g |
| POTASSIUM PHOSPHATE DIBASIC | 1.0 g |
| AMMONIUM NITRATE | 1.0 g |

TABLE 2-continued

| | |
|---|---|
| IRON (III) CHLORIDE HEXAHYDRATE | 0.05 g |
| SODIUM CHLORIDE | 20.0 g |
| DISTILLED WATER | 1000 ml |
| pH | 6.5–7.0 |

TABLE 3

| | |
|---|---|
| FLUID PARAFFIN (LIGHT) | 10.0 g |
| AMMONIUM NITRATE | 0.1 g |
| POTASSIUM PHOSPHATE DIBASIC | 1.0 g |
| MAGNESIUM SULFATE HEPTAHYDRATE | 0.2 g |
| IRON (III) CHLORIDE HEXAHYDRATE | 0.05 g |
| CALCIUM CHLORIDE | 0.02 g |
| YEAST EXTRACT | 0.01 g |
| SODIUM CHLORIDE | 20.0 g |
| DISTILLED WATER | 1000 ml |
| pH | 6.5–7.0 |

A sample was collected from the foregoing culture solution, and absorbance of 610 nm light was measured using a spectrophotometer (Shimadzu Corporation model UV-1200), yielding mixed bacteria which were in the steady period after culturing for seven days. The bacteria count of the resulting mixed bacteria was computed by measuring absorbance of 610 nm light by the bacteria suspension using the spectrophotometer.

The quantity of an n-hexane extract fraction, that is, the quantity of saturated hydrocarbons deriving from the fluid paraffin remaining in the culture solution, was measured in the following manner.

First, the culture solution was extracted twice by using 100 ml of n-hexane, and 100 ml of the extracted culture solution was passed through a column of sodium sulfate anhydride, whereby the culture solution was dehydrated and the bacteria was removed therefrom and concentrated. The resulting product was then purified by active alumina chromatography (active alumina: 200 mesh, 60 ml, Wako Pure Chemical Industries, Ltd.; glass column: Pyrex™ Glass, 20 mm×600 mm, flow rate: 20 ml/h), thereby removing metabolites such as fatty acid. Then the resulting product was dried (60° C. in the presence of air flow) until it reached a constant weight. Here, the weight of the dried product was treated as the quantity of an n-hexane extract fraction, i.e., the quantity of residual saturated hydrocarbon.

The quantity of the n-hexane extract fraction was determined by means of gas chromatography. Analysis conditions for the gas chromatography were as follows:

| | |
|---|---|
| Column: | SUPPORT PETROCOL B COLUMN (SUPELCO) |
| Oven temp.: | 50° C. to 350° C., 10° C./min |
| Injector temp.: | 300° C. |
| Detection temp.: | 360° C. |
| Detector: | FID |
| Carrier gas: | helium |

Further, degree of emulsification of the fluid paraffin into the culture solution was measured by removing the bacteria from the culture solution by means of centrifuge separation (3500 rpm; 20 min.), and then measuring the absorbance of the supernatant of light having a wavelength of 610 nm.

From five kinds of samples obtained through the foregoing first and second screenings, the mixed bacteria having the fastest fluid paraffin emulsification rate and the smallest n-hexane extract fraction quantity after culturing for seven days was obtained. This was a saturated hydrocarbon degrading bacteria group obtained from seawater, and included the FERMBP-7046 Acinetobacter strain (TFBOL-1), the FERMBP-7049 Acinetobacter strain (TFBOL-7), the FERMBP-7047 Pseudomonas strain (TFBOL-2), and the FERMBP-7048 Alcaligenes strain (TFBOL-3).

Next, each strain was isolated from the saturated hydrocarbon degrading bacteria group obtained in the above manner. Here, the isolating culture mediums used were a hydrocarbon plate culture medium and a common agar culture medium, obtained by the method proposed by Baruah et al. (Toru KODAMA, *Methods of Separating Microorganisms*, R & D Planning Co.). The hydrocarbon plate culture medium was obtained by the following steps:

putting the fluid paraffin in a powder form in advance by letting the fluid paraffin be absorbed into silica gel;

making a slurry of the paraffin powder by suspension in a small quantity of water; and mixing the slurry homogeneously with an agar culture medium prepared by adding 2% by weight of agar to the basic salt culture medium shown in Table 2 above.

A culture solution including the saturation hydrocarbon degrading bacteria group was applied onto the foregoing isolating culture medium by spraying, and cultured for 48 hours at 27° C. Then, expressed colonies were collected and cultured for two to three days at 37° C., whereby four strains, that is, bacteria TFBOL-1, TFBOL-2, TFBOL-3, and TFBOL-7, were obtained as the strains according to the present invention.

Subsequently, each isolated strain according to the present invention was identified in accordance with the method disclosed in *Bergey's Manual of Determinative Bacteriology*, 9th Edition.

In identifying the bacteria TFBOL-1 through TFBOL-8, the genus and species were found by conducting physiological experiments for each of (1) morphological characteristics including configuration of nutrient cells, polymorphism of the cell, maneuverability, and presence of spores; and (2) physiological characteristics including Gram's staining, catalase reaction, oxidase reaction, fermentation (generation of acid or gas from sugars) as well as development under anaerobic and aerobic conditions. The results are set forth in Table 4 below.

TABLE 4

| CHARACTERISTICS | TFBOL | | | | | | | |
|---|---|---|---|---|---|---|---|---|
| | 1 | 2 | 3 | 4 | 5 | 6 | 7 | 8 |
| GRAM'S STAINING | − | − | − | − | − | − | − | − |
| CELL POLYMORPHISM | R | R | R | R | R | R | R | R |
| MANEUVERABILITY | − | + | + | − | − | − | − | − |
| DEVELOPMENT UNDER: | | | | | | | | |
| AEROBIC CONDITIONS | + | + | + | + | + | + | + | + |
| ANAEROBIC CONDITIONS | − | + | − | − | − | − | − | − |
| CATALASE REACTION | + | + | + | + | + | + | + | + |
| OXIDASE REACTION | − | + | + | + | + | + | − | + |
| ACID GENERATION FROM SUGARS OF TEST | + O | + O | − − | + O | + O | + O | + O | − − |

(+: POSITIVE; −: NEGATIVE; S: SPHERICAL; R: ROD; O: OXIDATION)

Table 4 shows that the strains TFBOL-1 and TFBOL-7 were Gram negative short bacilli having no maneuverability, which did not grow under anaerobic conditions, and which showed positive in the catalase reaction, negative in the oxidase reaction, and O (oxidation) in the fermentation test (Oxidation-Fermentation Test). Based on these results, the TFBOL-1 TFBOL-7 strains were identified as bacteria of the genus Acinetobacter.

The strains TFBOL-1 and TFBOL-7 were domestically deposited with the National Institute of Bioscience and Human Technology of the Agency of Industrial Science and Technology (AIST) (1-3 Higashi 1-chome, Tsukuba-shi, Ibaraki-ken, Japan 305-8566) on Feb. 24, 1999, and were assigned Accession Nos. FERMP-17233 and FERMP-17236, respectively.

The strains TFBOL-1 and TFBOL-7 were later internationally deposited with the National Institute of Bioscience and Human Technology of AIST on Feb. 23, 2000 and were assigned Accession Nos. FERMBP-7046 and FERMBP-7049, respectively.

The strain TFBOL-2 was a Gram negative short bacillus having maneuverability, which developed under anaerobic conditions and showed positive in both the catalase reaction and oxidase reaction, and O in the OF test. Based on these results, the TFBOL-2 strain was identified as bacteria of the genus Pseudomonas.

The strain TFBOL-2 was domestically deposited with the National Institute of Bioscience and Human Technology of AIST on Feb. 24, 1999 and assigned Accession No. FERMP-17234.

Later, the TFBOL-2 strain was internationally deposited with the National Institute of Bioscience and Human Technology of AIST on Feb. 23, 2000 and assigned Depository No. FERMBP-7047.

The strain TFBOL-3 was a Gram negative short bacillus having maneuverability, which did not develop under anaerobic conditions, showed positive in both the catalase reaction and oxidase reaction, and did not generate acid from glucose. Based on these results, the TFBOL-3 strain was identified as bacteria of the genus Alcaligenes.

The strain TFBOL-3 was domestically deposited with the National Institute of Bioscience and Human Technology of AIST on Feb. 24, 1999 and assigned Accession No. FERMP-17235.

Later, the strain TFBOL-3 was internationally deposited with the National Institute of Bioscience and Human Technology of AIST on Feb. 23, 2000 and assigned Accession No. FERMBP-7048.

The strains TFBOL-4, TFBOL-5, and TFBOL-6 were Gram negative short bacilli having no maneuverability, which did not develop under anaerobic conditions, and showed positive both in the catalase reaction and oxidase reaction, and O in the OF test. Based on these results, the strains TFBOL-4, -5, and -6 were identified as bacteria of the genus Flavobacterium.

The strains TFBOL-4, TFBOL-5, and TFBOL-6 were internationally deposited with the National Institute of Bioscience and Human Technology of AIST on Feb. 23, 2000 and assigned Accession Nos. FERMBP-7050, FERMBP-7051, and FERMBP-7052, respectively.

The strain TFBOL-8 was a Gram negative short bacillus having no maneuverability, which did not develop under anaerobic conditions, showed positive in both the catalase reaction and oxidase reaction, and did not produce acid from glucose. Based on these results, the TFBOL-8 strain was identified as bacteria of the genus Moraxella.

The strain TFBOL-8 was internationally deposited with the National Institute of Bioscience and Human Technology of AIST on Feb. 23, 2000 and assigned Accession No. FERMBP-7053.

Of the above bacteria according to the present invention, the FERMBP-7046 strain of Acinetobacter (TFBOL-1), the FERMBP-7047 strain of Pseudomonas (TFBOL-2), the FERMBP-7048 strain of Alcaligenes (TFBOL-3), and the FERMBP-7049 strain of Acinetobacter (TFBOL-7) show activity in degrading saturated hydrocarbons present in oil components such as heavy oil when used individually, and also when used as necessary in a bacteria mixture.

Also, of the above bacteria, the FERMBP-7050 strain of Flavobacterium (TFBOL-4), the FERMBP-7051 strain of Flavobacterium (TFBOL-5), the FERMBP-7052 strain of Flavobacterium (TFBOL-6), and the FERMBP-7053 strain of Moraxella (TFBOL-8) show excellent degradation activity when mixed with at least one of the TFBOL-1, TFBOL-2, TFBOL-3, and TFBOL-7 and used as the bacteria mixture.

In particular, in decomposing saturated hydrocarbons present in oil components such as heavy oil, it is especially preferable to use a bacteria mixture containing all of TFBOL-4, -5, -6, and -8 and TFBOL-1, -2, -3, and -7.

Herein, "bacteria mixture" means a mixture including at least two different kinds of bacteria.

In the bacteria mixture according to the present invention, the Flavobacterium strain TFBOL-4, the Flavobacterium strain TFBOL-5, the Flavobacterium strain TFBOL-6, and the Moraxella strain TFBOL-8, either individually or in combination, may be included in the foregoing bacteria mixture as necessary.

Each of the strains TFBOL-4, TFBOL-5, TFBOL-6, and TFBOL-8 has poor activity in degrading saturation hydrocarbon when used alone, but it was found that when these strains are added to the bacteria TFBOL-1, -2, -3, or -7 or to the bacteria mixture according to the present invention, the bacteria or bacteria mixture shows better activity in degrading saturated hydrocarbons, for the same bacteria count, than when these strains are not added.

The mechanism of why degrading activity is improved by adding these strains is not clear. However, it is presumed that, while the bacteria or bacteria mixture of the present invention degrades saturated hydrocarbons, the TFBOL-4, -5, -6, and -8 strains degrade other oil components, such as aromatic hydrocarbons.

A heavy oil degrading bacteria nurturing composition of the present invention essentially includes 40 to 90 wt % of ammonium nitrate, 1 to 50 wt % of potassium phosphate dibasic, 2 to 50 wt % of magnesium sulfate, 1 to 20 wt % of iron (III) chloride, 0.2 to 15 wt % of calcium chloride, and 0.1 to 10 wt % of yeast extract as effective components.

The concentration of ammonium nitrate is preferably in a range from 60 through 80 wt %, and more preferably in a range from 70 through 75 wt %.

The concentration of potassium phosphate dibasic is preferably in a range from 2 through 25 wt %, and more preferably in a range from 5 through 10 wt %.

The concentration of magnesium nitrate is preferably in a range from 4 through 25 wt %, and more preferably in a range from 10 through 20 wt %.

The concentration of iron (III) chloride is preferably in a range from 2 through 10 wt %, and more preferably in a range from 3 through 5 wt %.

The concentration of calcium chloride is preferably in a range from 0.6 through 5 wt % and more preferably in a range from 1 through 3 wt %.

The concentration of yeast extract is preferably in a range from 0.2 through 3 wt % and more preferably in a range from 0.5 through 1 wt %.

The foregoing heavy oil degrading bacteria nurturing composition is used suitably as a component of a nutrient salt culture medium to culture and store microorganisms including bacteria, actinomyces, yeast, etc. having the ability to degrade hydrocarbons such as heavy oil. This heavy oil degrading bacteria nurturing composition is particularly suitable when included in a nutrient salt culture medium used to culture and store the bacteria and bacteria mixture according to the present invention.

For example, when the bacteria and bacteria mixture of the present invention are to be used as heavy oil degrading bacteria, the heavy oil degrading bacteria nurturing composition is made into an aqueous solution by dilution with 500 to 2000 times its weight of water, seawater, etc. Then, the bacteria or bacteria mixture are cultured in or added to the aqueous solution in a quantity and at a concentration which allows expression of heavy oil degrading activity, and by allowing the same to act on an object of treatment, such as heavy oil, the heavy oil can be removed through degradation. The concentration of the heavy oil degrading bacteria nurturing composition in the aqueous solution is not especially limited. However, as was mentioned, it is preferable to dissolve or dilute the same with 500 to 2000 times its weight of water or seawater.

It is also possible to remove heavy oil through degradation by adding the heavy oil degrading bacteria nurturing composition alone or in the form of the aqueous solution, without adding the bacteria or bacteria mixture, to earth and sand with e.g. heavy oil attached thereto. In other words, the degradation of hydrocarbons contained in the heavy oil can be promoted by growing and activating microorganisms present in the earth and sand using the heavy oil degrading bacteria nurturing composition.

As noted above, the essential components function sufficiently even in small amounts. Also, the heavy oil itself can be used as a carbon source for growing the heavy oil degrading bacteria, thus making some other carbon source, such as peptone, unnecessary. Thus, the heavy oil degrading bacteria nurturing composition can be prepared at a lower cost than with the conventional method, and is particularly useful as a culture medium to grow and store a large volume of heavy degrading bacteria.

The nutrient salt culture medium including the heavy oil degrading bacteria nurturing composition may additionally include inorganic compounds such as salts, or organic compounds such as fluid paraffin, where necessary.

When an aqueous solution of the dissolved or diluted heavy oil degrading bacteria nurturing composition is used, pH of the aqueous solution can be set arbitrarily depending on the kind of microorganisms used. However, pH is preferably in a range from 5.0 through 8.0, more preferably in a range from 6.0 through 7.5, and most preferably in a range from 6.5 through 7.0.

Examples of objects of treatment by the bacteria, bacteria mixture, heavy oil degrading bacteria nurturing composition, or formulation according to the present invention include: saturated hydrocarbons having 17–40 carbon atoms; aromatic hydrocarbons such as benzene, toluene, and naphthalene; heavy oil including the above saturated hydrocarbons or aromatic hydrocarbons and other kinds of oil components; etc.

A formulation according to the present invention is a formulation which contains the heavy oil degrading bacteria nurturing composition alone, or in a combination with the bacteria or bacteria mixture, other kinds of microorganisms having the heavy oil degrading ability, water, etc. The form of the formulation is not especially limited, and it can be in the form of pellets, sheets, balls, etc.

Specifically, starch, cellose, zeolite, vermiculite, sponge, etc. can be impregnated with, for example, an aqueous solution of the heavy oil degrading bacteria nurturing composition and the bacteria or bacteria mixture, and formed into pellets or sheets, or formed into solid form as balls, or sealed in a capsule having biodegradability.

The present formulation is used to degrade and remove heavy oil by spreading (scattering, etc.) these pellets or balls of the formulation over the beach where the heavy oil was washed ashore, and leaving for a time sufficient for degradation of the heavy oil to proceed. By using pellets, balls, or capsules of the formulation, the heavy oil degrading bacteria nurturing composition and the bacteria or bacteria mixture solidified in the formulation gradually washed into the object of treatment. In this manner, the degrading action to the e.g. heavy oil can be maintained for a considerably long time.

By using the formulation of the present invention as has been discussed, heavy oil can be removed through degradation efficiently over a wide area by quite simple operations.

The formulation may be scattered manually, or using a machine such as a sower where necessary.

The form of the object of treatment, from which oil components such as heavy oil are to be removed through degradation by using the bacteria, bacteria mixture, heavy oil degrading bacteria nurturing composition, or formulation according to the present invention is not especially limited. Examples of the object of treatment include heavy oil leaked to the ocean surface due to a shipwreck, earth and sand with heavy oil attached thereto, structures such as a vessel with heavy oil attached thereto, a reef with heavy oil attached thereto, etc.

In a method of treating oil components according to the present invention, at least one of the bacteria, bacteria mixture, heavy oil degrading bacteria nurturing composition, and formulation is added directly to the object having the oil components such as heavy oil, and left for a sufficiently long time for the degradation of the heavy oil to proceed. Alternatively, an object of treatment such as earth or sand can be treated by placing the earth or sand with e.g. heavy oil attached thereto in a column, and adding a solution containing the bacteria, bacteria mixture, and heavy oil degrading bacteria nurturing composition from the top of the column.

The temperature of the foregoing treatment is preferably in a range from 15° C. through 45° C., more preferably in a range from 20° C. through 35° C., and most preferably in a range from 22° C. through 28° C.

More specifically, examples of the present method of treating oil components include: a method in which a culture solution including the bacteria or bacteria mixture grown to the steady period is directly added to the object; a method in which only a solution including the heavy oil degrading bacteria nurturing composition is directly added to the object; a method in which the heavy oil degrading bacteria nurturing composition additionally including the bacteria or bacteria mixture is directly added to the object; and a method in which the foregoing solution is added to a container filled with the object, such as earth and sand.

When removing oil components such as heavy oil through degradation, the number of bacteria in the bacteria or bacteria mixture according to the present invention is not especially limited. However, a preferable range is from $1\times10^6$ to $1\times10^9$ per 1 g of the object with heavy oil attached thereto.

Second Embodiment

As discussed in the first embodiment above, earth and sand with oil components such as heavy oil attached thereto can be treated using at least one of the bacteria strain, bacteria mixture, heavy oil degrading bacteria nurturing composition, and formulation containing that composition, according to the present invention. This treatment yields treated substance from which the heavy oil has been degraded, leaving recycled sand.

The present embodiment investigates whether it is possible to use the sand obtained as treated substance by the foregoing treatment (hereinafter referred to as "recycled sand") as an aggregate or supplementary material in asphalt concrete for road paving or in cement mortar, i.e., whether the recycled sand can be practically used as a building and civil engineering material. The specific investigations made will be discussed in the Examples below.

As a result, with respect to use of the recycled sand as asphalt concrete for road paving, the foregoing investigations yielded the following results.

Specifically, when a recycled sand A, obtained by treating sand with 7% by weight of heavy oil attached thereto using a nutrient salt culture medium containing the foregoing heavy oil degrading bacteria nurturing composition and bacteria mixture for 56 days, and a recycled sand B, obtained by treating sand with 7% by weight of heavy oil attached thereto using only the nutrient salt culture medium containing the foregoing heavy oil degrading bacteria nurturing composition, were each dried in a bulk drier and added to an aggregate for asphalt concrete in the amount of 15% of the total aggregate, it was found that the aggregates obtained thereby easily met standards for asphalt concrete for road paving.

Incidentally, the results of the Examples to be discussed below indicate that the foregoing aggregates met standards for asphalt concrete for road paving with a margin to spare. Accordingly, an aggregate containing the recycled sand A or the recycled sand B in the amount of 20% to 30% of the total aggregate can also be expected to be applicable in asphalt concrete for road paving.

When one of the foregoing aggregates is used in asphalt concrete for road paving, it is generally heated to no less than 160° C. during application. For this reason, the bacteria or bacteria mixture in a live state, contained in the treated substance left after treatment of earth or sand, etc. are completely killed by the heating at the time of application of the asphalt concrete for road paving. This is because bacteria or bacteria mixtures are usually killed at approximately 60° C. Further, even in spore form they are killed at temperatures above 120° C. Accordingly, it is safe to assume that at temperatures of 160° C. and over, bacteria or bacteria mixtures will be completely killed.

As a result, it is sanitary to use the foregoing aggregates in asphalt concrete for road paving, and the biological influence of bacteria or bacteria mixtures on the asphalt concrete for road paving can be eliminated.

Next, with respect to use of the recycled sand in cement mortar, the foregoing investigations yielded the following results.

Specifically, a recycled sand A, obtained by treating sand with 7% by weight of heavy oil attached thereto using a nutrient salt culture medium containing the foregoing heavy oil degrading bacteria nurturing composition and bacteria mixture for 56 days, and a recycled sand B, obtained by treating sand with 7% by weight of heavy oil attached thereto using only the nutrient salt culture medium containing the foregoing heavy oil degrading bacteria nurturing composition, were each dried in a bulk drier and used as aggregate for cement mortar in the amount of 100% of the total aggregate, and the performance thereof was confirmed by tests such as a uniaxial compression test and a flexural test.

As a result, it was found that the foregoing aggregates were quite satisfactory for use in a mid-grade cement mortar. Accordingly, it can be expected that the foregoing aggregates could also be used as a supplementary aggregate in a high-grade cement mortar.

With regard to the relationship between the recycled sand A and the recycled sand B, the cement mortar using the recycled sand A (sand treated with nutritive salt culture and bacteria mixture) was of slightly better quality.

The present embodiment explained use of recycled sand obtained by treating sand with 7% by weight of heavy oil attached thereto using a nutrient salt culture medium containing the foregoing heavy oil degrading bacteria nurturing composition and bacteria mixture, or using only the nutrient salt culture medium containing the foregoing heavy oil degrading bacteria nurturing composition, for 56 days, but the present invention is not necessarily limited to this. It is also possible to use a recycled sand obtained by treatment for around 21 days, based on FIG. 2(b).

Further, when using recycled sand obtained by treating sand with 3% by weight of heavy oil attached thereto using a nutrient salt culture medium containing the foregoing heavy oil degrading bacteria nurturing composition and bacteria mixture, or using only the nutrient salt culture medium containing the foregoing heavy oil degrading bacteria nurturing composition, for 56 days, it goes without saying that the sand with 3% by weight of heavy oil attached thereto can be treated even more effectively than the sand with 7% by weight of heavy oil attached thereto.

Incidentally, the maximum quantity of heavy oil attached to sand is around 10% by weight of heavy oil; oil in excess of this quantity will be washed away without becoming attached. Accordingly, investigation of recycled sand obtained by treating sand with 7% by weight of heavy oil attached thereto is sufficient for practical purposes. Further, oil components are degraded even with sand with 10% by weight of heavy oil attached thereto, and thus recycled sand obtained thereby can be used as a building and civil engineering material.

Further, the present embodiment explained use of a treated substance obtained by treatment using a nutrient salt culture medium containing the foregoing heavy oil degrading bacteria nurturing composition and bacteria mixture, or using only the nutrient salt culture medium containing the foregoing heavy oil degrading bacteria nurturing composition, but a treated substance obtained by treating earth and sand with heavy oil attached thereto using at least one of the bacteria strain, bacteria mixture, and formulation according to the present invention can also be used as an aggregate or supplementary material in asphalt concrete for road paving or in cement mortar, i.e., as a building and civil engineering material.

EXAMPLES

Using the preparatory culture medium shown in Table 2 above or the nutrient salt culture medium shown in Table 5 below as the heavy oil degrading bacteria nurturing composition according to the present invention, and using crude oil (Arabian light oil) as the degradation substrate, quantity of oil components degraded was measured for each of the bacteria TFBOL-1, -2, -3, and -7 according to the present invention, as follows.

TABLE 5

| | |
|---|---|
| AMMONIUM NITRATE | 1.0 g |
| POTASSIUM PHOSPHATE DIBASIC | 0.1 g |
| MAGNESIUM SULFATE HEPTAHYDRATE | 0.2 g |
| IRON (III) CHLORIDE HEXAHYDRATE | 0.05 g |
| CALCIUM CHLORIDE | 0.02 g |
| YEAST EXTRACT | 0.01 g |
| SODIUM CHLORIDE | 20.0 g |
| DISTILLED WATER | 1000 ml |
| pH | 6.5–7.0 |

Example 1

First, TFBOL-1 bacteria were planted in the preparatory culture medium shown in Table 2 above and cultured by shaking (120 strokes/min.; 5 cm) at 25° C. for four days, yielding a preparatory culture solution. Next, bacteria were collected from the preparatory culture solution by centrifuge separation (3500 rpm; 20 min.), washed twice with a sterilized preparatory culture medium, and suspended in 1 ml of the preparatory culture medium, yielding 1 ml of a bacteria suspension (bacteria count $10^9$/ml).

To prepare the main culture solution, the foregoing crude oil was added to the nutritive salt culture medium shown in Table 5 in the amount of 1% by weight, which then underwent autoclave sterilization at 121° C. for 20 min. Then 1 ml of the foregoing bacteria suspension was inoculated into 100 ml of the main culture solution (in a shaking flask of 500 ml capacity), and was cultured by shaking (120 strokes/min.; 5 cm) at 30° C. for 10 days. Bacteria count of the TFBOL-1 bacteria after culturing for 10 days was $6.5 \times 10^9$.

After culturing for 10 days, the main culture solution was subjected to extraction twice, using 100 ml of chloroform per 100 ml of culture solution each time. An extract obtained thereby was sent through a column filled with anhydrous sodium nitrate to perform dehydration and cell-body elimination, yielding a chloroform extract fraction. This chloroform extract fraction was dried (60° C.; in presence of air flow) until it reached a constant weight, and this dry weight was treated as a quantity of crude oil remaining.

A biodegradation rate was calculated as a quantity of degradation substrate lost through degradation (%) with respect to the quantity of the degradation substrate (quantity of crude oil) prior to bacteria inoculation (100%).

Biodegradation rates were also calculated for each of the bacteria TFBOL-2 through -8 by the same method as described above. The results are shown in Table 6.

TABLE 6

| STRAIN | BIODEGRADATION RATE (%) |
|---|---|
| TFBOL-1 | 21.1 |
| TFBOL-2 | 28.8 |
| TFBOL-3 | 32.4 |
| TFBOL-4 | — |
| TFBOL-5 | — |
| TFBOL-6 | — |
| TFBOL-7 | 27.6 |
| TFBOL-8 | — |

In Table 6, values are omitted for bacteria strains which, having low degradation ability for comparatively high-molecule hydrocarbons, showed biodegradation rates of less than 10%.

As is evident from Table 6, the bacteria TFBOL-1, TFBOL-2, TFBOL-3, and TFBOL-7 showed high biodegradation rates of over 10%, indicating that they had high heavy oil degrading activity.

Example 2

Biodegradation rate was measured by performing the same operations as in Example 1 above, except that the bacteria suspension was obtained by suspending $0.5 \times 10^9$ each of TFBOL-1, TFBOL-2, TFBOL-3, and TFBOL-7 bacteria in 1 ml of the foregoing preparatory culture medium. The results are shown in Table 7 below.

Example 3

Biodegradation rate was measured by performing the same operations as in Example 1 above, except that the bacteria suspension was obtained by suspending $0.7 \times 10^9$ each of the bacteria TFBOL-1 through TFBOL-8 in 1 ml of basic salt culture medium. The results are shown in Table 7 below.

TABLE 7

| STRAIN | BIODEGRADATION RATE (%) |
|---|---|
| EXAMPLE 2 | 32.3 |
| EXAMPLE 3 | 52.5 |

As is evident from Table 7, a bacteria mixture including the bacteria TFBOL-1, TFBOL-2, TFBOL-3, and TFBOL-7, each of which exhibited a high biodegradation rate of over 10%, showed a biodegradation rate of over 10%, indicating a high heavy oil degrading activity. Further, a bacteria mixture including all of the bacteria TFBOL-1 through TFBOL-8 showed an even higher biodegradation rate, indicating a high heavy oil degrading activity.

Example 4

A chloroform extract fraction using a bacteria mixture according to the present invention was obtained by performing the same operations as in Example 2 above. Crude oil remaining in the chloroform extract fraction was separated out by alumina chromatography (activated alumina: 200 mesh, 60 ml, Wako Pure Chemical Industries, Ltd.; glass column: 20×600 mm Pyrex™ glass, flow rate 20 ml/h) and classified into saturated hydrocarbons, aromatic hydrocarbons, asphaltene, and column residue (hereinafter referred to as "Sa," "Ar," "As," and "Re," respectively). The Sa fraction obtained in this way was analyzed by gas chromatography using a predetermined method. Analysis conditions of the gas chromatography were as follows:

| | |
|---|---|
| Column: | Ultra ALLOY Capillary Column DX30 (15 m, 0.5 m) |
| Oven temp.: | 100° C. (0 min) to 250° C. (30 min), 4° C./min |
| Injector temp.: | 250° C. |
| Detection temp.: | 250° C. |
| Detector: | FID |
| Carrier gas: | helium |

Figure 1B:
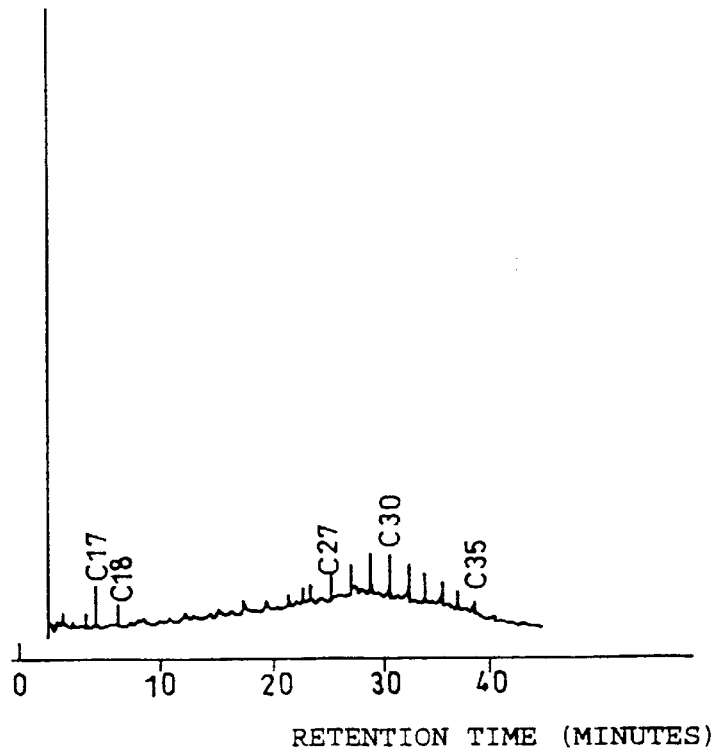
FIG. 1(b) is an explanatory drawing showing an elution pattern obtained by gas chromatography analysis, which illustrates degradation and removal of saturated hydrocarbon components contained in heavy oil by a bacteria mixture according to the present invention, showing the state after degradation.

FIGS. 1(a) and 1(b) are explanatory drawings showing elution patterns for Sa fractions of equal quantity before and after treatment, using a common scale intensity on the vertical axis. As shown in FIGS. 1(a) and 1(b), using a bacteria mixture according to the present invention can degrade all saturated hydrocarbons having less than 35 carbon atoms, which are crude oil components.

Example 5

Figure 2A:
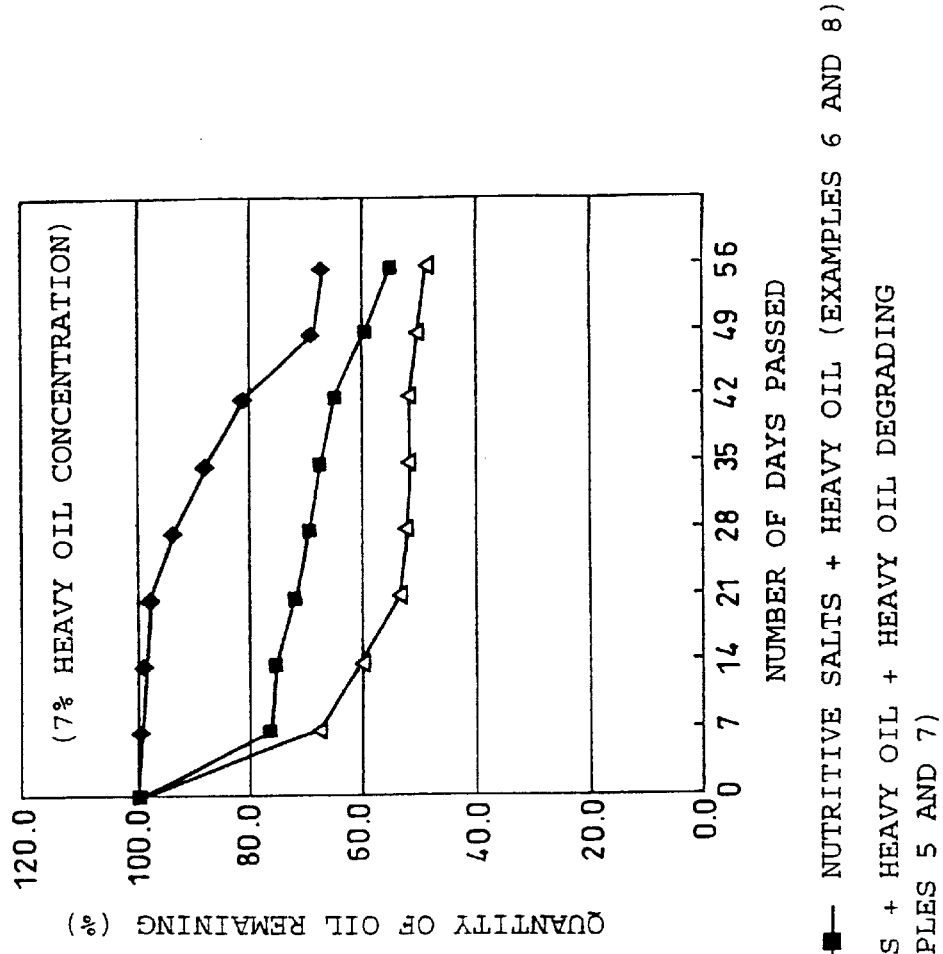
FIG. 2(a) is a graph showing change over time in a quantity of oil remaining when sand containing 3% by weight of heavy oil attached thereto is treated using a bacteria mixture or a heavy oil degrading bacteria nurturing composition according to the present invention.

1 kg of sand containing 3% by weight of heavy oil C as the heavy oil was mixed with 100 ml of a nutritive salt culture medium having the composition shown in Table 5 above as a heavy oil decomposing bacteria nurturing composition according to the present invention, and with $1 \times 10^9$ each of the bacteria TFBOL-1 through TFBOL-8 as a bacteria mixture according to the present invention. After mixing, the sand was placed in a bag and buried at the seashore, and every seven days a predetermined quantity of the sand was sampled and a remaining oil quantity (quantity of oil remaining) was measured using the same method of measuring remaining crude oil quantity as in Example 1 above. Considering the quantity of oil in the sand containing 3% by weight of heavy oil on the first day (prior to treatment) as 100%, change over time of the quantity of oil remaining was investigated by calculating a quantity of oil remaining (%) once every seven days. The results are shown in FIG. 2(a). Further, an Sa fraction was obtained for the sand sampled on the 7th and 56th days by performing the same operations as in Example 4 above, which was then analyzed by gas chromatography. The results are shown in FIGS. 3(a) through 3(c). FIGS. 3(a) through 3(c), and FIGS. 4(a) through 4(c) to be discussed below, like FIGS. 1(a) and 1(b) above, are explanatory drawings which use a common scale intensity on the vertical axis. Further, as a control, change over time of an equal quantity of untreated sand was also investigated. The results for the control are also shown in FIG. 2(a).

Example 6

Sand containing 3% by weight of heavy oil was treated using the same method as in Example 5 above, except that the foregoing bacteria mixture was not added, and change over time in quantity of oil remaining was investigated and an Sa fraction was analyzed by gas chromatography. The results are shown in FIG. 2(a) and in FIGS. 4(a) through 4(c).

Examples 7 and 8

Figure 2B:
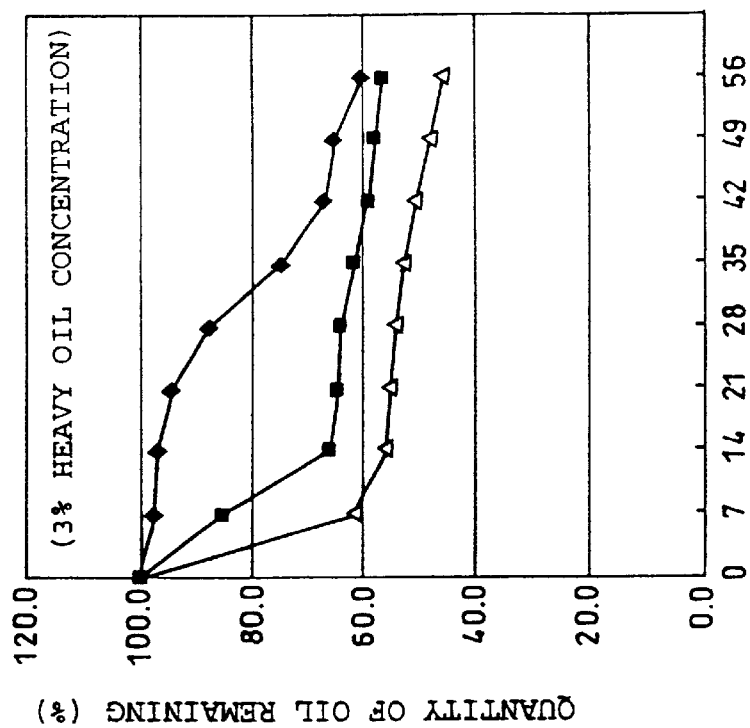
FIG. 2(b) is a graph showing change over time in a quantity of oil remaining when sand containing 7% by weight of heavy oil attached thereto is treated using a bacteria mixture or a heavy oil degrading bacteria nurturing composition according to the present invention.

Using the same methods as in Examples 5 and 6 above, sand containing 7% by weight of heavy oil was treated, and change over time in quantity of oil remaining was investigated. The results are shown in FIG. 2(b). An Sa fraction was also analyzed by gas chromatography.

As shown in FIG. 2(a), at a point 14 days after commencing the experiment, the quantity of oil remaining in the untreated sand containing 3% by weight of heavy oil (the control) had decreased by only 3.1%. In contrast, in the sand treated using only the nutritive salt culture medium containing the heavy oil degrading bacteria nurturing composition (Example 6), quantity of oil remaining was decreased by 34%, and in the sand treated using both the nutritive salt culture medium containing the heavy oil degrading bacteria nurturing composition and the bacteria mixture (Example 5), there was a sharp decrease of 44% in quantity of oil remaining.

Further, as shown in FIG. 2(b), at a point 21 days after commencing the experiment, the quantity of oil remaining in the untreated sand containing 7% by weight of heavy oil (the control) had decreased by only 2.3%. In contrast, in the sand treated using only the nutritive salt culture medium containing the heavy oil degrading bacteria nurturing composition (Example 8), quantity of oil remaining was decreased by 28%, and in the sand treated using both the nutritive salt culture medium containing the heavy oil degrading bacteria nurturing composition and the bacteria mixture (Example 7), there was a sharp decrease of 46.7% in quantity of oil remaining.

As the foregoing results show, rate of heavy oil degradation was fastest with treatment using both the nutritive salt culture medium containing the heavy oil degrading bacteria nurturing composition and the bacteria mixture, and treatment using only the nutritive salt culture medium containing the heavy oil degrading bacteria nurturing composition showed the next fastest rate of heavy oil degradation. From this it is evident that with treatment using both the nutritive salt culture medium containing the heavy oil degrading bacteria nurturing composition and the bacteria mixture, heavy oil degradation proceeded at a high rate due to the bacteria mixture, and with treatment using only the nutritive salt culture medium containing the heavy oil degrading bacteria nurturing composition, heavy oil degradation proceeded at a high rate due to the growth and activity of hydrocarbon degrading bacteria ordinarily present on seashores, promoted by the heavy oil degrading bacteria nurturing composition.

Incidentally, in the heavy oil C used in the foregoing experiment, quantities of saturated hydrocarbons and aromatic hydrocarbons of low boiling point which dissolve in water or evaporate are so small as to be insignificant. For this reason, the quantity of loss of such saturated hydrocarbons and aromatic hydrocarbons of low boiling point can be disregarded.

Further, as shown in FIGS. 3(a) through 3(c) and 4(a) through 4(c), treatment using both the nutritive salt culture medium containing the heavy oil degrading bacteria nurturing composition and the bacteria mixture, or treatment using only the nutritive salt culture medium containing the heavy oil degrading bacteria nurturing composition, degraded all saturated hydrocarbons having less than 35 carbon atoms, which are crude oil components, and this degradation was especially rapid with treatment using both the nutritive salt culture medium containing the heavy oil degrading bacteria nurturing composition and the bacteria mixture.

Example 9

1 kg of sand containing 3% by weight of heavy oil C as the heavy oil was mixed with 100 ml of a nutritive salt culture medium having the composition shown in Table 5 above, which contains a heavy oil decomposing bacteria nurturing composition, and with $1 \times 10^9$ each of the TFBOL-1, -2, -3, and -7 bacteria as a bacteria mixture according to the present invention. After mixing, the sand was placed in a bag and buried at the seashore, and a predetermined quantity of the sand was sampled on the first day (prior to treatment) and after 14 days.

The sampled sand was classified into Sa, Ar, As, and Re fractions in the same manner as in Example 4 above, and each fraction obtained in this way was analyzed by gas chromatography in order to measure change in the heavy oil components in the sand containing 3% by weight of heavy oil. Analysis conditions of the gas chromatography were as follows:

| | |
|---|---|
| Column: | Ultra ALLOY Capillary Column DX30 (15 m, 0.5 m) |
| Oven temp.: | 100° C. (0 min) to 250° C. (30 min), 4° C./min |
| Injector temp.: | 250° C. |

-continued

| | |
|---|---|
| Detection temp.: | 250° C. |
| Detector: | FID |
| Carrier gas: | helium |

Example 10

Sand containing 3% by weight of heavy oil was treated using the same method as in Example 9 above, except that the foregoing bacteria mixture was not added, in order to measure change in the heavy oil components in the sand due to action of the nutritive salt culture medium containing the heavy oil degrading bacteria nurturing composition according to the present invention.

As shown in FIG. 5(a), at a point 14 days after commencing the experiment, use of the bacteria mixture according to the present invention (Example 9) had greatly degraded the Sa fraction. Further, treatment using only the nutritive salt culture medium containing the heavy oil degrading bacteria nurturing composition according to the present invention (Example 10) showed the second greatest degradation of the Sa fraction after treatment using the bacteria mixture.

Example 11

Using the same method as in Example 9 above, sand containing 7% by weight of heavy oil was treated, and change in the heavy oil components was measured after 21 days. The results are shown in FIG. 5(b).

Example 12

Sand containing 7% by weight of heavy oil was treated using the same method as in Example 11 above, except that the foregoing bacteria mixture was not added, in order to measure change in the heavy oil components in the sand due to action of the heavy oil degrading bacteria nurturing composition according to the present invention.

As shown in FIGS. 5(a) and 5(b), at a point 14 days or 21 days after commencing the experiment, use of the bacteria mixture according to the present invention (Examples 9 and 11) had greatly degraded the Sa fraction. Further, treatment using only the nutritive salt culture medium containing the heavy oil degrading bacteria nurturing composition according to the present invention (Examples 10 and 12) showed the second greatest degradation of the Sa fraction after treatment using the bacteria mixture.

Example 13

The present embodiment will discuss the results of an investigation of whether sand (hereinafter referred to as "recycled sand") obtained by treating sand with heavy oil attached thereto using a nutritive salt culture medium containing the foregoing heavy oil degrading bacteria nurturing composition and a bacteria mixture, or using only the nutritive salt culture medium containing the foregoing heavy oil degrading bacteria nurturing composition can be used in asphalt concrete for road paving.

This investigation was carried out by performing an experiment regarding whether asphalt concrete containing the recycled sand as a supplementary aggregate meets the standards for asphalt concrete for road paving.

Two kinds of recycled sand were used: recycled sand A, obtained by treating sand with 7% by weight of heavy oil attached thereto using a nutrient salt culture medium containing the foregoing heavy oil degrading bacteria nurturing composition and a bacteria mixture for 56 days, and a recycled sand B, obtained by treating sand with 7% by weight of heavy oil attached thereto using only the nutrient salt culture medium containing the foregoing heavy oil degrading bacteria nurturing composition.

The aggregate blending conditions were as shown in Table 8 below. Specifically, in blend 1, recycled sand A made up 15% of the total aggregate, and in blend 2, recycled sand B made up 15% of the total aggregate. Further, blend 3 shows typical blending conditions in conventional asphalt concrete for road paving, in which neither recycled sand A nor recycled sand B is used. Here, recycled sands A and B were dried in a bulk drier at 11° C. for 24 hours, and heated at 180° C. for 16 hours.

TABLE 8

| AGGREGATE MATERIAL | BLEND 1 (%) | BLEND 2 (%) | BLEND 3 (%) |
|---|---|---|---|
| NO. 6 CRUSHED ROCK | 38 | 38 | 38 |
| NO. 7 CRUSHED ROCK | 15 | 15 | 15 |
| SCREENINGS (SC) | 13 | 13 | 17 |
| COARSE SAND | 5 | 5 | 5 |
| FINE SAND | 9 | 9 | 13 |
| RECYCLED SAND A | 15 | — | — |
| RECYCLED SAND B | — | 15 | — |
| ROCK POWDER | 5 | 5 | 5 |

Next, Table 9 shows the respective particle sizes of each of the aggregate materials listed above prior to blending.

TABLE 9

| SCREEN SIZE (mm) | CRUSHED ROCK (%) NO. 6 | CRUSHED ROCK (%) NO. 7 | SC (%) | SAND (%) COARSE | SAND (%) FINE | RECYCLED SAND (%) A | RECYCLED SAND (%) B | ROCK POWDER (%) |
|---|---|---|---|---|---|---|---|---|
| 19 | 100.0 | | | | | | | |
| 13.2 | 91.5 | 100.0 | | 100.0 | 100.0 | 100.0 | 100.0 | |
| 4.75 | 1.4 | 93.6 | 100.0 | 98.3 | 99.8 | 99.7 | 99.9 | |
| 2.36 | 0.7 | 13.6 | 83.8 | 91.2 | 99.0 | 49.9 | 54.4 | |
| 0.6 | 0.6 | 1.1 | 36.4 | 60.2 | 92.0 | 22.5 | 24.3 | 100.0 |
| 0.3 | | 0.8 | 23.9 | 20.0 | 62.4 | 17.6 | 20.0 | 97.0 |
| 0.15 | | | 16.0 | 3.3 | 2.4 | 3.2 | 2.5 | 92.0 |
| 0.075 | | | 9.4 | 1.5 | 0.7 | 0.3 | 0.2 | 72.0 |

Further, Table 10 shows the respective particle size distributions for each of the blends 1, 2, and 3 compounded of the aggregate materials having the respective particle sizes shown in Table 9 above. Each of these satisfies the general specifications for asphalt concrete for road paving set forth in the right-most column of Table 10.

TABLE 10

| SCREEN SIZE (mm) | BLEND 1 (%) | BLEND 2 (%) | BLEND 3 (%) | STANDARD PARTICLE SIZE RANGE (%) |
|---|---|---|---|---|
| 19 | 100 | 100 | 100 | 100 |
| 13.2 | 96.8 | 96.8 | 96.8 | 95–100 |
| 4.75 | 61.4 | 61.4 | 61.0 | 55–70 |
| 2.36 | 39.2 | 39.9 | 40.0 | 35–50 |
| 0.6 | 24.8 | 25.0 | 26.6 | 18–30 |
| 0.3 | 17.3 | 17.7 | 18.3 | 10–21 |
| 0.15 | 7.5 | 7.4 | 7.7 | 6–16 |
| 0.075 | 5.0 | 5.0 | 5.4 | 4–8 |

Next, Table 11 shows mixing conditions and compaction conditions for asphalt concrete for road paving. Here, the asphalt used was "straight asphalt 60 to 80" defined in JIS K 2207 "Petroleum Asphalt." Straight asphalt 60 to 80 has a needle penetration at 25° C. of more than 40 but no more than 60.

TABLE 11

| ITEM | CONDITIONS |
|---|---|
| ASPHALT QUANTITY | 5.8% |
| AGGREGATE HEATING TEMPERATURE | TARGET 160° C.–170° C. |
| ASPHALT HEATING TEMPERATURE | TARGET 150° C.–160° C. |
| MIXING TEMPERATURE | TARGET 152° C.–157° C. |
| COMPACTION TEMPERATURE | TARGET 140° C.–145° C. |
| NUMBER OF COMPACTIONS | 50 TIMES EACH ON FRONT AND BACK |

Tests performed, in addition to apparent density, were a flow test, a Marshall stability test, and a residual stability test, as stipulated in the general specifications for asphalt concrete for road paving. Conditions for the Marshall stability test and the residual stability test were as shown in Table 12 below.

TABLE 12

| ITEM | CONDITIONS |
|---|---|
| MARSHALL STABILITY TEST (AS PER ASPHALT PAVING SPECIFICATIONS) | CURING TEMP.: 60° C. CURING TIME: 30 MINUTES |
| RESIDUAL STABILITY TEST (AS PER ASPHALT PAVING SPECIFICATIONS) | CURING TEMP.: 60° C. CURING TIME: 48 HOURS |

The results of tests performed under the foregoing conditions are shown in Table 13 below.

TABLE 13

| ITEM | BLEND 1 | BLEND 2 | BLEND 3 | STANDARD VALUES |
|---|---|---|---|---|
| APPARENT DENSITY (g/cm$^3$) | 2.373 | 2.378 | 2.364 | — |
| FLOW VALUE (¹⁄₁₀₀ cm) | 29.3 | 23.0 | 24.7 | 20–40 |
| STABILITY (Kg) | 1031.7 | 1008.3 | 935.0 | ≧500 |
| RESIDUAL STABILITY (%) | 93.7 | 94.4 | 98.2 | ≧75 |

TABLE 13-continued

| ITEM | BLEND 1 | BLEND 2 | BLEND 3 | STANDARD VALUES |
|---|---|---|---|---|
| VISUAL OBSERVATION DURING TEST | SOME ASPHALT SEEPAGE DURING PREPARATION OF SPECIMEN | — | — | |

The results in Table 13 show that both blend 1, which used recycled sand A, and blend 2, which used recycled sand B, satisfy standard values for quality of asphalt concrete for road paving.

In other words, it was found that both an aggregate containing as supplementary aggregate 15% of the recycled sand A, obtained by treating sand with 7% by weight of heavy oil attached thereto using a nutritive salt culture medium containing the heavy oil degrading bacteria nurturing composition according to the present invention and a bacteria mixture for 56 days, and an aggregate containing as supplementary aggregate 15% of the recycled sand B, obtained by treating sand with 7% by weight of heavy oil attached thereto using only the nutritive salt culture medium containing the heavy oil degrading bacteria nurturing composition according to the present invention for 56 days, can be used in asphalt concrete for road paving.

Example 14

The present embodiment will discuss the results of an investigation of whether recycled sand obtained by treating sand with heavy oil attached thereto using the foregoing bacteria or bacteria mixture can be used in cement mortar.

This investigation used the two kinds of recycled sand used in Example 13 above, i.e. the recycled sand A, obtained by treating sand with 7%. by weight of heavy oil attached thereto using a nutritive salt culture medium containing the heavy oil degrading bacteria nurturing composition according to the present invention and a bacteria mixture for 56 days, and the recycled sand B, obtained by treating sand with 7% by weight of heavy oil attached thereto using only the nutritive salt culture medium containing the heavy oil degrading bacteria nurturing composition according to the present invention for 56 days. In order to apply the recycled sand A and the recycled sand B to cement mortar, each type of recycled sand was mixed with cement as an aggregate to prepare a specimen for strength tests, and then uniaxial compression strength and flexural strength of this specimen were measured. These tests were carried out as stipulated in JIS R 5201 "Methods of Performing Physical Testing of Cement."

Particle size distributions of the recycled sand A and the recycled sand B were as shown in Table 14 below.

TABLE 14

| SCREEN SIZE (mm) | RECYCLED SAND A (%) | RECYCLED SAND B (%) |
|---|---|---|
| 13.2 | 100.0 | 100.0 |
| 4.75 | 99.7 | 99.9 |
| 2.36 | 49.9 | 54.4 |
| 0.6 | 22.5 | 24.3 |
| 0.3 | 17.6 | 20.0 |
| 0.15 | 3.2 | 2.5 |
| 0.075 | 0.3 | 0.2 |

With regard to the method of performing the strength tests, a form for preparing the specimen was made up of three forms of 4×4×16 cm each, connected together. The specimen was obtained by mixing ordinary Portland cement with aggregate and water at an aggregate/cement ratio (S/C) of 2 and a water/cement ratio (W/S) of 65%. Prior to pouring the mixed cement mortar into the form, a flow test was performed.

The specimen was prepared using the above form, and removed from the form the next day. After weighing the specimen, water curing was commenced by placing the specimen in a water bath at 20° C.±3° C. The specimen was taken out of the bath after seven days and after 28 days, at which time it was weighed, and a uniaxial compression test and a flexural test were performed thereon.

Table 15 shows the results of the flow tests, and Table 16 the results of the strength tests. In the flow tests, a flow cone was filled with mixed cement and raised upwards. The flow values shown in Table 15 are abstract numbers expressing in mm the diameter of mortar spreading out from the base of the flow cone at this time.

TABLE 15

| FLOW VALUE | RECYCLED SAND A + CEMENT + WATER (S/C = 2; W/C = 65%) | RECYCLED SAND B + CEMENT + WATER (S/C = 2; W/C = 65%) |
|---|---|---|
| MAXIMAL VALUE | 221.8 | 235.4 |
| MINIMAL VALUE | 211.7 | 234.7 |

TABLE 16

| BLEND | SPECIMEN | IMMEDIATELY AFTER REMOVING FROM FORM WEIGHT (g) | AFTER 7 DAYS WEIGHT (g) | AFTER 7 DAYS COMPRESSION STRENGTH (N/mm$^2$) | AFTER 7 DAYS FLEXURAL STRENGTH (N/mm$^2$) | AFTER 28 DAYS WEIGHT (g) | AFTER 28 DAYS COMPRESSION STRENGTH (N/mm$^2$) | AFTER 28 DAYS FLEXURAL STRENGTH (N/mm$^2$) |
|---|---|---|---|---|---|---|---|---|
| 1 | 1 | 530.0 | 533.8 | 16.5 | 2.85 | — | — | — |
| | 2 | 532.3 | 535.9 | 16.5 | 2.95 | — | — | — |
| | 3 | 530.1 | 533.0 | 15.7 | 4.45 | — | — | — |
| | 4 | 529.3 | — | — | — | 539.2 | 23.5 | 5.68 |
| | 5 | 533.5 | — | — | — | 543.2 | 23.1 | 5.54 |
| | 6 | 529.6 | — | — | — | 539.0 | 23.7 | 5.59 |
| 2 | 7 | 526.7 | 536.0 | 15.6 | 2.62 | — | — | — |
| | 8 | 526.6 | 536.0 | 15.8 | 2.53 | — | — | — |
| | 9 | 527.4 | 537.0 | 15.8 | 2.62 | — | — | — |
| | 10 | 521.2 | — | — | — | 535.7 | 24.6 | 5.49 |
| | 11 | 519.9 | — | — | — | 534.4 | 23.4 | 5.01 |
| | 12 | 517.8 | — | — | — | 532.1 | 23.1 | 5.11 |

Standards stipulated by JIS for high-grade cement mortar specify compression strength values of not less than 14.71N/mm$^2$ at a material age of seven days, and not less than 29.42N/mm$^2$ at a material age of 28 days. Typical measured values for compression strength are around 25N/mm$^2$ at a material age of seven days, and around 41N/mm$^2$ at a material age of 28 days. Further, typical measured values for flexural strength are around 5N/mm$^2$ at a material age of seven days, and around 7N/mm$^2$ at a material age of 28 days.

In light of these values, the results in Table 16 above show that both cement mortar containing blend 1, which used recycled sand A, and cement mortar containing blend 1, which used recycled sand B, satisfied the standard of a compression strength value of not less than 14.71N/mm$^2$ at seven days. However, at 28 days, both showed compression strength values slightly less than the standard of 29.42N/mm$^2$.

With regard to flexural strength, both of the above cement mortars showed flexural strength values slightly less than the typical values for flexural strength of around 5N/mm$^2$ at seven days and around 7N/mm$^2$ at 28 days.

With regard to the relationship between the recycled sand A and the recycled sand B, the cement mortar using the recycled sand A showed slightly better strength.

The foregoing results indicate that a cement mortar in which the aggregate is entirely made up of the recycled sand A or the recycled sand B is fully adequate, not as a high-grade cement mortar, but as a mid-grade cement mortar.

Incidentally, the foregoing test results were obtained using aggregates entirely made up of the recycled sand A or the recycled sand B; a cement mortar using recycled sand as a supplementary aggregate, as in the asphalt concrete for road paving in Example 13, can be expected to be fully satisfactory for use as a high-grade cement mortar.

As discussed above, the novel strain of bacteria according to the present invention having a heavy oil degrading ability may be FERMBP-7046, a strain belonging to the genus Acinetobacter.

Further, as discussed above, the novel strain of bacteria according to the present invention having a heavy oil degrading ability may be FERMBP-7049, a strain belonging to the genus Acinetobacter.

Further, as discussed above, the novel strain of bacteria according to the present invention having a heavy oil degrading ability may be FERMBP-7047, a strain belonging to the genus Pseudomonas.

Further, as discussed above, the novel strain of bacteria according to the present invention having a heavy oil degrading ability may be FERMBP-7048, a strain belonging to the genus Alcaligenes.

As discussed above, a bacteria mixture according to the present invention may include at least one kind of bacteria having a heavy oil degrading ability selected from the group consisting of: FERMBP-7046, a strain of Acinetobacter; FERMBP-7049, a strain of Acinetobacter; FERMBP-7047, a strain of Pseudomonas; and FERMBP-7048, a strain of Alcaligenes.

The foregoing bacteria or bacteria mixture was discovered when bacteria were isolated from seawater in order to discover a strain having a hydrocarbon degrading ability in nutrient-poor conditions as close as possible to those in the natural world. Thus, the above bacteria or bacteria mixture can be readily grown on inexpensive nutrition sources and degrade hydrocarbon efficiently. Accordingly, leaked oil components, for example, can be easily and efficiently removed through degradation at a low cost by using the foregoing bacteria or bacteria mixture.

As discussed above, a heavy oil degrading bacteria nurturing composition of the present invention may include 40 to 90 wt % of ammonium nitrate, 1 to 50 wt % of potassium phosphate dibasic, 2 to 50 wt % of magnesium sulfate, 1 to 20 wt %. of iron (III) chloride, 0.2 to 15 wt % of calcium chloride, and 0.1 to 10 wt % of yeast extract as effective components.

With this structure, the heavy oil degrading bacteria nurturing composition can be prepared inexpensively, and can promote growth of heavy oil degrading bacteria and the activation of heavy oil degradation. Consequently, leaked oil components, for example, can be removed through degradation inexpensively, simply, and effectively by causing the heavy oil degrading bacteria nurturing composition to act on the oil components by e.g. scattering the heavy oil degrading bacteria nurturing composition alone, or in an aqueous solution prepared by dissolving it in 500 to 2000 times its weight of e.g. seawater, or with the addition of the foregoing bacteria mixture.

As discussed above, the formulation according to the present invention may include the foregoing heavy oil degrading bacteria nurturing composition.

Further, as discussed above, the formulation according to the present invention may include one or more of the foregoing heavy oil degrading bacteria or the foregoing bacteria mixture and the heavy oil degrading bacteria nurturing composition set forth in claim 6 hereinbelow.

With this structure, oil components in an object of treatment such as sand can be degraded by simple operations such as scattering the object of treatment with the present formulation, prepared, for example, by dissolving the foregoing bacteria or bacteria mixture, the foregoing heavy oil degrading bacteria nurturing composition, etc. in an aqueous solution, or forming the same into pellets, or impregnating the same into an organic material in sheet form.

As discussed above, a method of treating oil components according to the present invention uses at least one of: one or more of the foregoing oil degrading bacteria, the foregoing bacteria mixture, the foregoing heavy oil bacteria nurturing composition, and the foregoing formulation.

With this method, the above bacteria or bacteria mixture can be readily grown on inexpensive nutrition sources and degrade hydrocarbon efficiently. Accordingly, leaked oil components, for example, can be easily and efficiently removed through degradation at a low cost.

As discussed above, a building and civil engineering material according to the present invention may contain a treated substance obtained by treating earth and sand with heavy oil attached thereto using at least one of: one or more of the foregoing oil degrading bacteria, the foregoing bacteria mixture, the foregoing heavy oil bacteria nurturing composition, and the foregoing formulation.

With this structure, in a treated substance obtained by treating earth and sand with heavy oil attached thereto using at least one of the bacteria, bacteria mixture, heavy oil degrading bacteria nurturing composition, and formulation according to the present invention, the heavy oil has been degraded, leaving recycled sand. Further, this recycled sand is suitable for use as a building and civil engineering material.

Consequently, by using at least one of the foregoing bacteria, bacteria mixture, heavy oil degrading bacteria nurturing composition, and formulation to treat earth and sand containing heavy oil washed ashore from e.g. a tanker which has run aground, a treated substance (recycled sand) can be obtained which is suitable for use as a building and civil engineering material, i.e., in asphalt concrete for road paving or in cement mortar.

As a result, earth and sand with heavy oil attached thereto, which conventionally were incinerated and buried, for example, can be recycled and provided for use as a building and civil engineering material.

The embodiments and Examples discussed in the foregoing detailed explanation serve solely to illustrate the technical details of the present invention, which should not be narrowly interpreted within the limits of such embodiments and concrete examples, but rather may be applied in many variations, provided such variations do not depart from the spirit of the present invention or exceed the scope of the patent claims set forth below.

What is claimed is:

1. A bacteria mixture comprising
    biologically pure cultures of FERMBP-7047, a strain of Pseudomonas bacteria;
    FERMBP-7046, a strain of Acinetobacter bacteria;
    FERMBP-7049, a strain of Acinetobacter bacteria;
    FERMBP-7048, a strain of Alcaligenes bacteria;
    FERMBP-7050, a strain of Flavobacterium bacteria;
    FERMBP-7051, a strain of Flavobacterium bacteria;
    FERMBP-7052, a strain of Flavobacterium bacteria; and
    FERMBP-7053, a strain of Moraxella bacteria.

2. A method of removing heavy oil from an object coated with or containing heavy oil, comprising the steps of;
    (a) providing to the object a bacteria mixture comprising
        biologically pure cultures of FERMBP-7046, a strain of Acinetobacter bacteria;
        FERMBP-7049, a strain of Acinetobacter bacteria;
        FERMBP-7047, a strain of Pseudomonas bacteria;
        FERMBP-7048, a strain of Alcaligenes bacteria;
        FERMBP-7050, a strain of Flavobacterium bacteria;
        FERMBP-7051, a strain of Flavobacterium bacteria;
        FERMBP-7052, a strain of Flavobacterium bacteria; and
        FERMBP-7053, a strain of Moraxella bacteria; and
    (b) waiting a period of time that is sufficient for the bacteria to degrade the heavy oil, wherein the period of time is from about 7 days to about 56 days.

3. The method of claim 2, wherein the number of bacteria included in a bacteria mixture is from $1\times10^6$ to $1\times10^9$ per 1 g of the object.

4. The method of claim 2, wherein the providing step occurs in a range of temperature from 15° C. to 45° C.

5. The method of claim 2, wherein the pH of the bacteria mixture is from pH 5.0 to 8.0.

6. The method of claim 2, further comprising the step of diluting the bacteria mixture with 500 times to 2000 times its weight of water or seawater before the providing step.

7. A formulated bacteria mixture comprising
    a bacteria mixture consisting of
        biologically pure cultures of FERMBP-7047, a strain of Pseudomonas bacteria;
        FERMBP-7046, a strain of Acinetobacter bacteria;
        FERMBP-7049, a strain of Acinetobacter bacteria;
        FERMBP-7048, a strain of Alcaligenes bacteria;
        FERMBP-7050, a strain of Flavobacterium bacteria;
        FERMBP-7051, a strain of Flavobacterium bacteria;
        FERMBP-7052, a strain of Flavobacterium bacteria; and
        FERMBP-7053, a strain of Moraxella bacteria,
    and a bacteria nurturing composition containing 40–90 wt % of ammonium nitrate, 1–50 wt % of potassium phosphate dibasic, 2–50 wt % of magnesium sulfate, 1–20 wt % of iron (III) chloride, 0.2–15 wt % of calcium chloride, and 0.1–10 wt % of yeast extract.

* * * * *